(12) United States Patent
Yoon et al.

(10) Patent No.: US 9,827,004 B2
(45) Date of Patent: *Nov. 28, 2017

(54) SURGICAL DISC REMOVAL TOOL

(71) Applicant: GLOBUS MEDICAL, INC., Audubon, PA (US)

(72) Inventors: Samuel Yoon, Wyndmoor, PA (US); Ryan Agard, Royersford, PA (US); Jason Pastor, Philadelphia, PA (US); Sean Suh, Jamesburg, NJ (US); Daniel Waite, Pottstown, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 228 days.

This patent is subject to a terminal disclaimer.

(21) Appl. No.: 14/744,090

(22) Filed: Jun. 19, 2015

(65) Prior Publication Data

US 2015/0282833 A1    Oct. 8, 2015

Related U.S. Application Data

(63) Continuation-in-part of application No. 14/683,320, filed on Apr. 10, 2015, now Pat. No. 9,265,517, which is a continuation of application No. 14/319,895, filed on Jun. 30, 2014, now Pat. No. 9,028,517, which is a continuation of application No. 14/057,116, filed on Oct. 18, 2013, now Pat. No. 8,801,738, which is a continuation of application No. 13/362,440, filed on Jan. 31, 2012, now Pat. No. 8,585,726.

(51) Int. Cl.
*A61B 17/32* (2006.01)
*A61B 17/3207* (2006.01)
*A61B 17/00* (2006.01)

(52) U.S. Cl.
CPC ........... *A61B 17/320016* (2013.01); *A61B 17/32002* (2013.01); *A61B 17/320725* (2013.01); *A61B 17/320758* (2013.01); *A61B 17/320708* (2013.01); *A61B 2017/00261* (2013.01); *A61B 2017/00685* (2013.01); *A61B 2017/320064* (2013.01); *A61B 2017/320733* (2013.01); *A61B 2217/007* (2013.01)

(58) Field of Classification Search
CPC ...... A61B 17/320783; A61B 17/32002; A61B 17/320725; A61B 17/22; A61B 17/320016; A61B 2017/00261; A61B 2017/00685; A61B 2017/320733; A61B 2017/320024; A61B 2017/320028; A61B 2017/320032
See application file for complete search history.

(56) References Cited

U.S. PATENT DOCUMENTS 5,047,040 A    9/1991    Simpson et al.
5,217,479 A    6/1993    Shuler
(Continued)

*Primary Examiner* — Ashley Fishback

(57) ABSTRACT

A tissue removal device including customizable tips and method of use thereof. The tissue removal device may include an outer shaft having a removable tip attached to the outer shaft and a rotatable inner shaft extending through the outer shaft and having a rotatable cutting portion extending from the inner shaft. Disc material may be cut and removed from a surgical area using an auger-like and/or suction mechanism to facilitate the transfer of removed tissue away from the surgical area.

18 Claims, 10 Drawing Sheets

(56) References Cited

U.S. PATENT DOCUMENTS

| | | | |
|---|---|---|---|
| 5,320,635 A * | 6/1994 | Smith | A61B 17/32002 |
| | | | 408/713 |
| 5,569,284 A * | 10/1996 | Young | A61B 17/32002 |
| | | | 604/22 |
| 5,709,698 A | 1/1998 | Adams et al. | |
| 5,782,795 A | 7/1998 | Bays | |
| 6,042,593 A | 3/2000 | Storz et al. | |
| 6,183,433 B1 | 2/2001 | Bays | |
| 6,217,598 B1 | 4/2001 | Berman et al. | |
| 6,620,180 B1 | 9/2003 | Bays et al. | |
| 2011/0270294 A1 | 11/2011 | Rubin | |
| 2012/0053484 A1 | 3/2012 | Parks | |
| 2012/0101513 A1 | 4/2012 | Shadeck et al. | |
| 2012/0172905 A1 | 7/2012 | Lee Shee et al. | |
| 2012/0221035 A1 * | 8/2012 | Harvey | A61B 17/32002 |
| | | | 606/170 |

\* cited by examiner

SURGICAL DISC REMOVAL TOOL

CROSS REFERENCE TO RELATED APPLICATIONS

This patent application is a continuation-in-part of U.S. patent application Ser. No. 14/683,320, filed Apr. 10, 2015, which is a continuation of U.S. patent application Ser. No. 14/319,895, filed on Jun. 30, 2014, now U.S. Pat. No. 9,028,517, which is a continuation application of U.S. patent application Ser. No. 14/057,116 filed on Oct. 18, 2013, now U.S. Pat. No. 8,801,738, which is a continuation application of U.S. Ser. No. 13/362,440 filed on Jan. 31, 2012, now U.S. Pat. No. 8,585,726, the contents of these applications being incorporated herein in their entireties for all purposes.

BACKGROUND OF THE PRESENT DISCLOSURE

1. Field of the Present Disclosure

The present disclosure is generally directed to a surgical device. More specifically, the disclosure may be directed to a surgical device that facilitates the removal of tissue.

2. Related Art

A spine comprises a series of small bones referred to as vertebrae. Spinal discs are fixed in place between each pair of vertebrae and function like a pad or cushion to prevent the vertebrae from grinding against each other and permit the spine to be flexible. A variety of scenarios may exist where damage to one or more of these spinal discs may occur including, but not limited to, injury and illness. Severe, even debilitating, pain can result from such damage.

Surgical procedures exist that attempt to alleviate the pain that accompanies such damage. At least one of these procedures may involve the removal of at least a portion of tissue associated with a spinal disc. Many conventional devices currently exist on the market for facilitating the removal of tissue associated with a spinal disc. However, each conventional device suffers from one or more drawbacks.

Conventional devices exist which suffer from the problem of being purely manual. Such manual devices require the use of human muscle, which fatigues, to perform the procedure. Additionally, such manual devices require significantly more time to complete the procedure as opposed to devices which have one or more powered, or otherwise mechanical, components.

However, merely providing for a powered device that facilitates removal of tissue associated with a spinal disc does not completely remedy the drawbacks of conventional devices. Many existing powered disc removal devices require expensive capital equipment to power the device. Additionally, surgeons are reluctant to use powered devices designed for removal of at least a portion of tissue associated with a spinal disc because the devices are overpowered or lack proper safety measures.

Furthermore, conventional devices have drawbacks in their ability to remove tissue associated with the spinal disc that has been severed. Typically, existing devices, whether manual or powered, rely solely on suction manufactured by generated airflow in order to remove tissue associated with a spinal disc that has been cut. Such an approach includes various drawbacks, including requiring a device capable of generating the suction. This requires at least the extra capital expense of purchasing a device capable of generating the requisite suction.

Accordingly, there is a need for device that improves a surgeon's ability to remove at least a portion of tissue associated with a spinal disc without relying solely on suction generated by airflow.

SUMMARY OF THE PRESENT DISCLOSURE

The present disclosure meets the foregoing need of improving a surgeon's ability to remove at least a portion of tissue associated with a spinal disc without relying solely on suction generated by airflow.

Accordingly, one aspect of the present disclosure describes a tissue removal device. The tissue removal device may include an outer shaft and a threaded shaft. The tissue removal device may include a customizable tip. The customizable tip serves to increase the versatility of the tissue removal device by providing a choice of a specific shaft, cutting instrument, or both in order to customize the tissue removal device.

At least one aspect of the disclosure may include a shaft cutting tool that emerges from an end of an outer shaft. Another aspect of the disclosure may include a flexible cutting blade extending from a threaded shaft. Threaded shaft may be driven by a driving mechanism in order to provide an auger-like suction mechanism to facilitate the transfer of removed tissue to a collection chamber that is coupled to the outer shaft and threaded shaft.

According to another aspect of the present disclosure the collection chamber includes at least a partial enclosure. At least a portion of this enclosure includes transparent material that allows for the inspection of the inside of the collection chamber. Additionally, the collection chamber may comprise a pluggable hole and/or a pluggable port that may aid in providing versatility to a surgeon utilizing the tissue removal device.

According to another aspect of the present disclosure, the flexible cutting blade may be expanded or contracted. Expanding or contracting the flexible cutting blade may increase or decrease the cutting diameter of the flexible cutting blade. In accordance with this feature, one aspect of the disclosure may include a window on the handle of the tissue removal device. The window may provide a visual indicator as to the height of the flexible cutting blade.

According to yet another aspect, the tissue removal device may include an outer shaft having a removable tip attached to the outer shaft and a rotatable inner shaft extending through the outer shaft and having a cutting portion extending from the inner shaft. The inner shaft may be straight or angled, thereby forming a straight or angled tissue removal device. If angled, the inner shaft may include a spring region in the form or a relief or spiral cut to angle the inner shaft. A base of the cutting portion may be offset relative to an outer diameter of the outer shaft to allow an enlarged gap between the cutting portion and the outer shaft. The enlarged gap may be configured to create a non-coaxial exit path for the cut portion of the tissue in the tip.

The removable tip may come in different forms. For example, the tip may include a curette in the form of a lip radially extending outward around an entire circumference of the tip. Alternatively, the tip may include a curette, a blunt distal end, and an open window in the distal end. The tip may be provided with a plurality of teeth configured to provide a scissor-like effect when the cutting portion rotates against the plurality of teeth.

According to another aspect, a method for removing tissue using a tissue removal device may include accessing an area for tissue removal; cutting a portion of tissue at a surgical site by rotating the cutting portion of the inner shaft; and conveying the cut portion of tissue away from the surgical site through a space between the outer shaft and the inner shaft. The cut portion of tissue may be conveyed via suction and/or by an auger-like mechanism if the inner shaft is threaded.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION OF THE PRESENT DISCLOSURE

Figure 1:
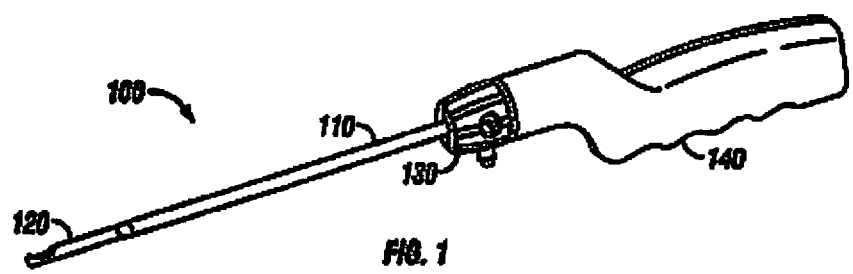
FIG. 1 shows a tissue removal device, according to an aspect of the present disclosure.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The present disclosure is generally directed to a surgical device. More specifically, the disclosure may be directed to a device, used by a surgeon, to facilitate the removal of tissue.

The word "surgeon", as used in this disclosure, means any person that uses the disclosure to either sever tissue or attempt to sever tissue. Such a person may be educated, certified, and trained to perform surgical procedures involving the removal of tissue. Such a person may also be a lay person with no experience in the surgical field. In addition, such a person may have a skill-set, education, and/or knowledge base which falls somewhere between a person who is educated, certified, and trained to perform surgical procedures and a lay person.

The word "tissue", as used in this disclosure, means any tissue associated with a spinal disc. Such tissue can comprise many forms, including tissue from the inside of the disc referred to as the nucleus, tissue from the outside of the disc referred to as the annulus, or tissue associated with any other portion of a spinal disc. Such tissue may also comprise any tissue that resides in the surrounding area of the spine which is, or may reasonably cause, discomfort that may be associated with a spinal disc. Such tissue may also comprise any tissue that may be found in a carbon based life form.

FIG. 1 shows a tissue removal device according to an aspect of the present disclosure. The tissue removal device 100 may include an outer shaft 110, a customizable tip 120, collection chamber 130, and handle 140. The outer shaft 110 extends from the customizable tip 120 to the collection chamber 130. In at least one aspect of the present disclosure, outer shaft 110 may enclose a threaded shaft (not shown). Handle 140 provides a member that a surgeon may use for holding, controlling, and/or directing the tissue removal device. The handle 140 may include a variety of grips that may facilitate use and control of the tissue removal device 100, including, e.g., rubber, plastic, wood, metal, etc.

Customizable tip 120 provides tissue removal device 100 with increased versatility. Customizable tip 120 facilitates the altering of the tip of tissue removal device 100, as well as, the accompanying cutting instrument (discussed herein below). The customizable tip 120 may comprise either a tip, a cutting instrument, or both. When the customizable tip 120 does not include a cutting instrument, it is an aspect of the present disclosure that the corresponding outer shaft 110 or threaded shaft may be fitted with a cutting instrument as needed. The customizable tip 120 may be provided in, e.g., a sealed and sterilized packaging. The customizable tip 120 may be disposable.

Customizable tip 120 may be coupled to tissue removal device 100 in a plurality of different ways. For example, the customizable tip 120 and the outer shaft 110 may be constructed as a single, unibody structure that connects to the collection chamber 130 through a connector (discussed herein below).

The customizable tip 120 may be a detachable component that is designed to be coupled to the outer shaft 110, which extends to the collection chamber through a connector.

The customizable tip 120 may be designed to extend from the threaded shaft as either a unibody structure or as a detachable component. It is readily understood by one of ordinary skill in the art that the present disclosure need not be so limited. The customizable tip 120 may be coupled to the tissue removal device 100 in any manner which provides for the tip and/or cutting instrument of the tissue removal device 100 to be customized.

Figure 2A:
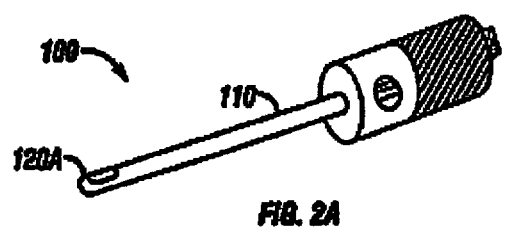
FIG. 2A shows an example of a customizable tip.
Figure 2B:
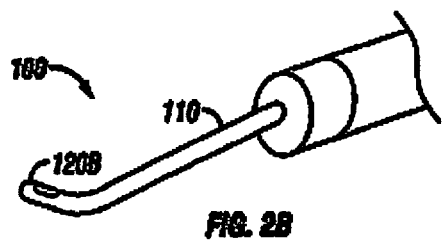
FIG. 2B shows another example of a customizable tip, which includes an angled portion.
Figure 2C:
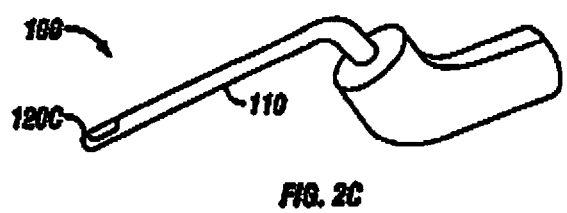
FIG. 2C shows yet another example of a customizable tip, which includes an angled portion.

FIGS. 2A, 2B, and 2C provide non-limiting examples of a variety of customizable tips 120 (120A, 120B, 120C, respectively).

FIG. 2A shows a customizable tip 120A that is similar to the customizable tip disclosed in FIG. 1, 120. As seen, the customizable tip 120A may include a substantially straight customizable tip. The customizable tip 120A is accompanied by the straight outer shaft 110. The outer shaft 110 may be mounted to (or through) the collection chamber. As seen in FIG. 2A, the collection chamber may have a housing that is substantially cylindrical in shape and the outer shaft 110 may be affixed to (or through) an end of the collection chamber.

FIG. 2B shows a customizable tip 120B that may be curved, angled, or otherwise formed, shaped or molded. The customizable tip 120B may be accompanied by the straight outer shaft 110 and the collection chamber.

FIG. 2C shows a customizable tip 120C that may be fitted to the tissue removal device 100, where the customizable tip 120C is accompanied by a curved outer shaft 110. The curved outer shaft 110 may be mounted to (or through) a curved collection chamber. As seen in FIG. 2C, an aspect of the disclosure contemplates that instead of the outer tip of outer shaft 110 being angled, the portion of outer shaft 110 which extends from the collection chamber 130, or other portion of tissue removal device 100 may be curved, angled, or otherwise shaped, formed, or molded in a manner which facilitates a more versatile tissue removal device 100.

Figure 3:
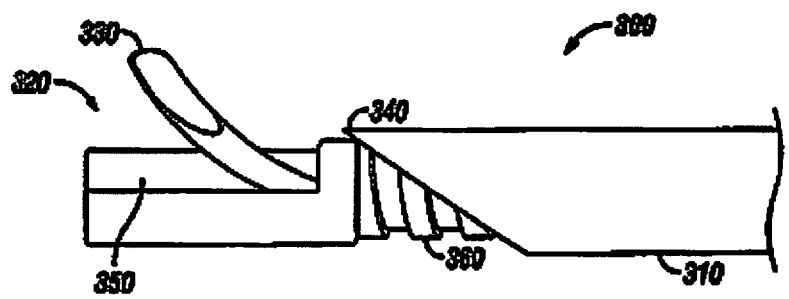
FIG. 3 shows an example of a cutting portion of a tissue removal device, according to an aspect of the present disclosure.
Figure 10:
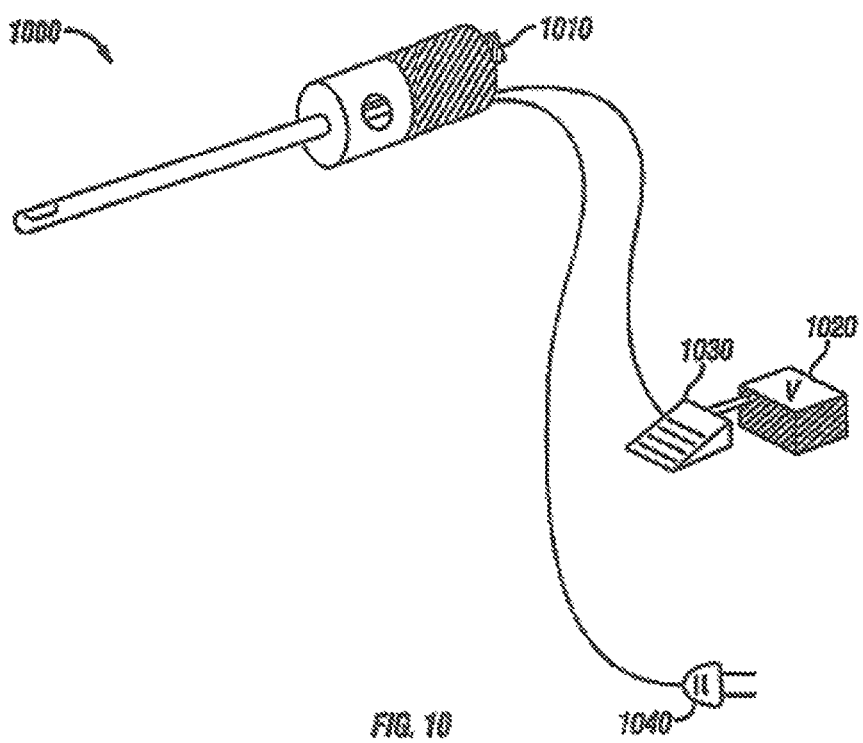
FIG. 10 shows a tissue removal system, including power connections and a tissue removal device.

FIG. 3 shows a cutting portion 300 of a tissue removal device (e.g., the tissue removal device 100, shown in FIG. 1, or the tissue removal device in the tissue removal system 1000, shown in FIG. 10). According to an aspect of the present disclosure, the tissue removal device (e.g., the tissue removal device 100, shown in FIG. 1) may include the cutting portion 300 in lieu of, or in addition to the customizable tip 120 and outer shaft 110. In the former case, the cutting portion 300 may be provided in the outer shaft 110 and configured to adjustably extend into an open section in the customizable tip 120, so as to contact and sever a tissue material. In the latter case, the cutting portion 300 may replace the customizable tip 120.

The cutting portion 300 includes a customizable tip 320 and an outer shaft 310. The cutting portion 300 may further include a shaft cutting tool 340. The customizable tip 320 may include a flexible cutting blade 330, a sample retriever 350, and a threaded shaft 360. The outer shaft 310 may encapsulate and guide the threaded shaft 360, as well as the customizable tip 320. The shaft cutting tool 340 may be integrally formed with the outer shaft 310, or it may be provided as a separate element that is connected to the outer shaft 310. The shaft cutting tool 340 and flexible cutting blade 330 provide two cutting mechanisms that are capable of severing material, including, e.g., tissue connected to a carbon based life form, thereby making tissue available for removal. The cutting blade 330 may be expanded or contracted to increase or decrease a cutting diameter. The adjustable cutting blade 330 allows a surgeon to accommodate varying patient anatomy and pathology. The severed tissue may be retrieved by the sample retriever 350. The threaded shaft 360, enclosed within the outer shaft 310, mechanically operates as a conveyor to move, convey, or transfer the severed tissue from the surgical site through the outer shaft 310 and into the collection chamber 130. The outer shaft 310 may be sized such that the tissue remains in contact with the threaded shaft 360 to prevent cutter portion 300 from jamming.

Figure 4:
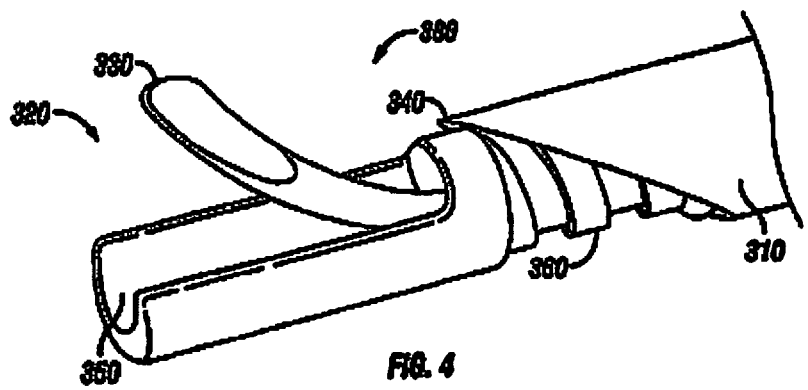
FIG. 4 shows an enlarged, perspective view of the cutting portion shown in FIG. 3.

FIG. 4 shows a perspective, enlarged view of the cutting portion 300. This enlarged view of the cutting portion 300 more clearly accents the features of the cutting portion 300 at the tip end of the device. As seen in FIG. 4, the shaft cutting tool 340 is configured to emerge from the end of the outer shaft 310, so that it may facilitate tissue severing. Shaft cutting tool 340 may function independently, or in conjunction with the flexible cutting blade 330, to provide a surgeon with improved control and precision in removing a desired portion of tissue.

In the cutting portion 300, the flexible cutting blade 330 may extend from an end of the threaded shaft 360, or another member (not shown) extending from the collection chamber 130. When extending from the end of the threaded shaft 360, flexible cutting blade 330 may revolve at the same rotational velocity as the threaded shaft 360 when driven by, e.g., a motor (not shown).

Flexible cutting blade 330 provides a surgeon with the advantage of accommodating carbon based life forms of varying anatomies and pathologies. This advantage is achievable by the configuration of the flexible cutting blade 330, which may be expandable and/or contractible for optimal positioning and severing of tissue. In this regard the cutting blade 330 may be extracted from the threaded shaft 360 to increase the cutting diameter or may be retracted into the threaded shaft 360 to reduce the cutting diameter. In other words, the cutting portion 300 may provide a surgeon with the ability to contract flexible cutting blade 330 in order to decrease its cutting diameter. Alternatively, or in combination, the cutting portion 300 may provide a surgeon with the ability to expand the length of flexible cutting blade 330 in order to increase its cutting diameter. Flexible cutting blade 330 may be made from, e.g., nitinol. However, it will be readily understood by one of ordinary skill in the art that the flexible cutting blade 330 of the present disclosure need not be so limited. The flexible cutting blade 330 of the present disclosure may be made of any material capable of severing tissue and providing the flexibility described herein, including, but not limited to, any metal, alloy, plastic, etc.

An aspect of the present disclosure provides a feature to accommodate precise use of flexible cutting blade 330. It will be readily understood by one of ordinary skill in the art that cutting portion 300 may be connected (directly or indirectly) to a handle similar to handle 140 of the tissue removal device 100. Accordingly, an aspect of the present disclosure provides that a window (not shown) may be cut into or formed in the handle 140. The window may provide a surgeon with a visual indicator as to the height of flexible cutting blade 330, thereby ensuring that the surgeon may more precisely use tissue removal device 100.

Additionally, the sample retriever 350 may function to retrieve the tissue that is removed by shaft cutting tool 340 and/or flexible cutting blade 330. This could happen in a plurality of ways. For example, either the shaft cutting tool 340 or the flexible cutting blade 330 may independently sever the tissue. This approach results in the tissue detaching from the carbon based life form and being collected in the sample retriever 350. Alternatively, or in combination, for example, the threaded shaft 360 may be mechanically retracted, thereby pulling the sample retriever 350 towards the collection chamber 130 through the outer shaft 310 which pushes flexible cutting blade 330 toward the sample retriever 350, thereby severing the tissue, and effectively trapping the tissue in the sample retriever 350. However, it will be readily understood by one of ordinary skill in the art that the present disclosure need not be so limited. As a result, other ways to sever and collect tissue for depositing in the collection chamber which fall within the spirit and scope of the invention may be realized in accordance with the present disclosure.

After tissue is severed and retrieved by sample retriever 350, threaded shaft 360 works as a conveyor to convey, move, or transfer the tissue away from the surgical site, through outer shaft 310, and into the collection chamber 130. Threaded shaft 360, enclosed by outer shaft 310, may be driven by a driving mechanism including, e.g., a motor (not shown). When driven by a driving mechanism, the threaded shaft 360 provides an alternative to conventional suction mechanisms that are generated purely based upon airflow. This alternative sample collection mechanism includes, e.g., the motor to revolve or rotate the threaded shaft 360 in order to provide an auger-like suction capability. The motor may be powered by a battery (see FIG. 10). Utilizing a motor to implement an auger-like suction mechanism provides the advantage of being able to power the tissue removal device 100 with batteries, while avoiding high cost capital equipment to drive a device that generates suction based on airflow. When flexible cutting blade 330 extends from the end of the threaded shaft 360, flexible cutting blade 330 may revolve at the same rotational velocity as threaded shaft 360 when driven by a motor (not shown). It is noted that the auger-like suction capability described herein above is driven by a motor. However, it would be readily understood by one of ordinary skill in the art that the auger-like suction capability of the present disclosure need not be so limited. As such, the auger-like suction capability of the present disclosure may be driven by other means, e.g., manually.

Figure 5:
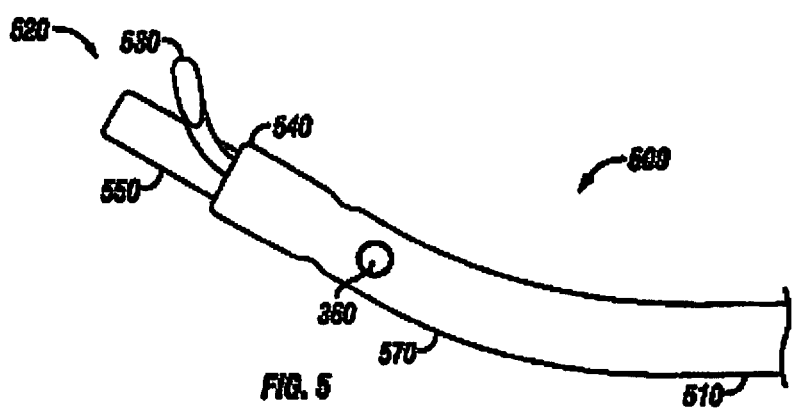
FIG. 5 shows another example of a cutting portion of a tissue removal device, according to an aspect of the present disclosure.

FIG. 5 shows another example of a cutting portion 500 of a tissue removal device (e.g., the tissue removal device 100, shown in FIG. 1, or the tissue removal device in the tissue removal system 1000, shown in FIG. 10). According to an aspect of the present disclosure, the tissue removal device (e.g., the tissue removal device 100, shown in FIG. 1) may include the cutting portion 500 in lieu of, or in addition to the customizable tip 120 and outer shaft 100. In the former case, the cutting portion 500 may be provided in the outer shaft 110 and configured to adjustably extend into an open section in the customizable tip 120, so as to contact and sever a tissue material. In the latter case, the cutting portion 500 may replace the customizable tip 120.

The cutting portion 500 may include a customizable tip 520, an angled shaft 570, and an outer shaft 510. The customizable tip 520 may include a flexible cutting blade 530, a shaft cutting tool 540, a sample retriever 550, and a threaded shaft 360. Angled shaft 570 may provide the cutting portion 500 with the capability of reaching a surgical site that is unreachable by, for example, the straight outer shaft 110 structure seen in FIG. 1.

The angled shaft 570 and the outer shaft 510 may be formed as a single unibody structure. Alternatively, the angled shaft 570 and outer shaft 510 may be formed from two or more parts, including, e.g., detachable components that may be coupled to each other.

Figure 6A:
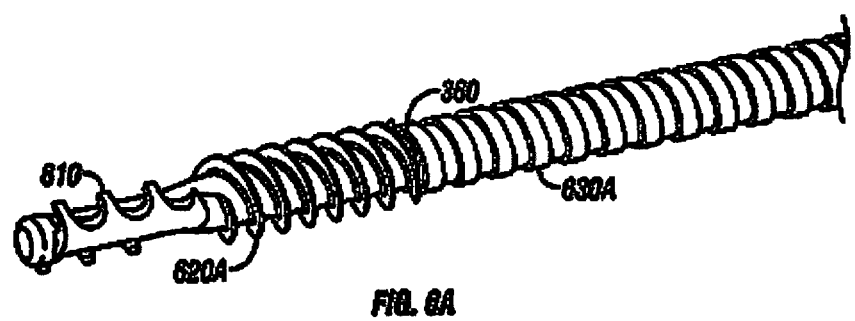
FIG. 6A shows a perspective view of a cutter shaft that may be used in another example of a cutting portion of a tissue removal device, according to an aspect of the present disclosure.

FIG. 6A shows an example of a cutter shaft that may be included within an outer shaft of a tissue removal device, such as, e.g., tissue removal device 100. A motor (not shown) may be provided to turn or revolve the threaded shaft 360, thereby providing an auger-like suction capability. Since cutter 610 extends from the end of threaded shaft 360, cutter 610 will rotate at the same rotational velocity as threaded shaft 360. The cutter may include one or more helical portions to move tissue to the next part of the threaded shaft 360, a sharp threaded section 620A. Threaded shaft 360 may comprise a plurality of sections, wherein each section provides a different threading. The threaded shaft 360 may be formed from a single piece of material, or from multiple pieces of materials.

As seen, the threaded shaft 360 may comprise the sharp threaded section 620A followed by a flatter threaded section 630A. The sharp threaded section 620A may provide better gripping and quicker transportation of particles. Once the tissue samples pass the threaded section 620A, the flatter threaded section 630A may be configured to receive the tissue samples and convey, move, or transfer the tissue samples to the collection chamber 130. The threaded section 620A may include, e.g., helical fins, to provide better gripping and quicker transportation of tissue samples from the cutter 610. The flatter threaded section 630A may include, e.g., helical patterns, to convey tissue from the threaded section 620A to, e.g., the collection chamber 130. It is noted that the threaded shaft 360 may include, for example, a single lead thread auger, a double lead thread auger (as shown in FIG. 6A), a triple lead thread auger, or a greater number of lead thread augers.

Figure 6B:
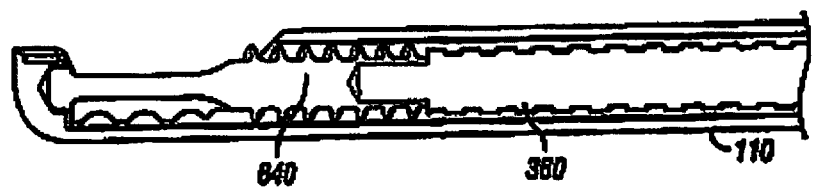
FIG. 6B shows a cross-section or cut-away view of another example of a cutting portion of a tissue removal device, including the cutter shaft of FIG. 6A.

FIG. 6B shows a cut-away view that illustrates a threaded shaft 360 (shown in FIG. 6A) being retracted in the outer shaft 110 towards the collection chamber 130. The threaded shaft 360 may engage the outer shaft 110 via an engagement mechanism 640, which may include, e.g., threading, grooves, channels, or the like. The motor drives the threaded shaft 360, forcing the threaded shaft 360 to revolve (or rotate) and interact with the engagement mechanism 640 to transport tissue from the cutter 610 to the collection chamber 130. In this manner, threaded shaft 360 functions to convey, move, or transfer tissue samples from the surgical site to the collection chamber 130. The outer shaft 110 may be sized so that a tissue sample will remain in contact with the threaded shaft 360 to prevent the auger-like suction mechanism from jamming.

Figure 6C:
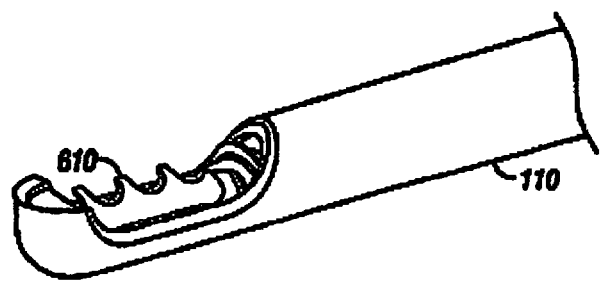
FIG. 6C shows a perspective view of the cutting portion of FIG. 6B.

FIG. 6C shows a perspective view of the cutter 610 residing within the outer shaft 110. Cutter 610 revolves at the same rotational velocity as its accompanying threaded shaft. When cutter 610 is revolving, and comes into contact with tissue, it severs one or more portions of tissue—i.e., one or more tissue samples—which are then conveyed, moved, or transferred to collection chamber 130 via the auger-like suction capability of, e.g., helical fin structure of the cutter 610, the sharp threaded section 620A, and the flatter threaded section 630A.

Figure 7A:
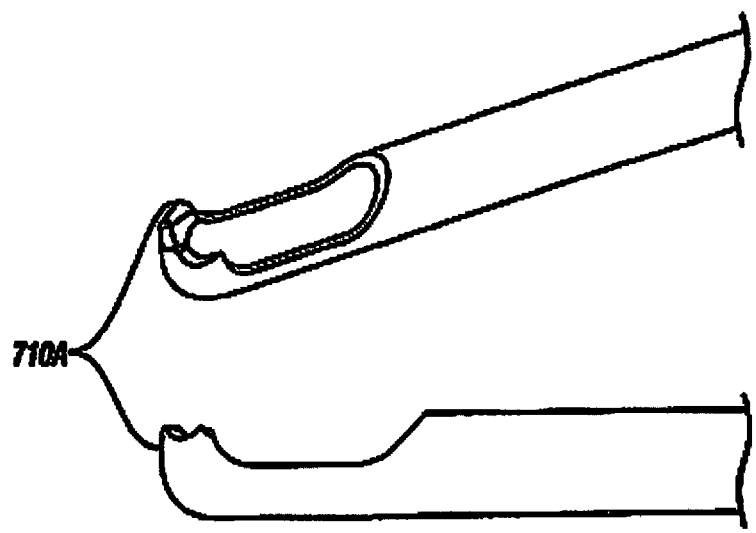
FIG. 7A shows a perspective view and a side view of a customized tip comprising a serrated curette tip shaft.
Figure 7B:
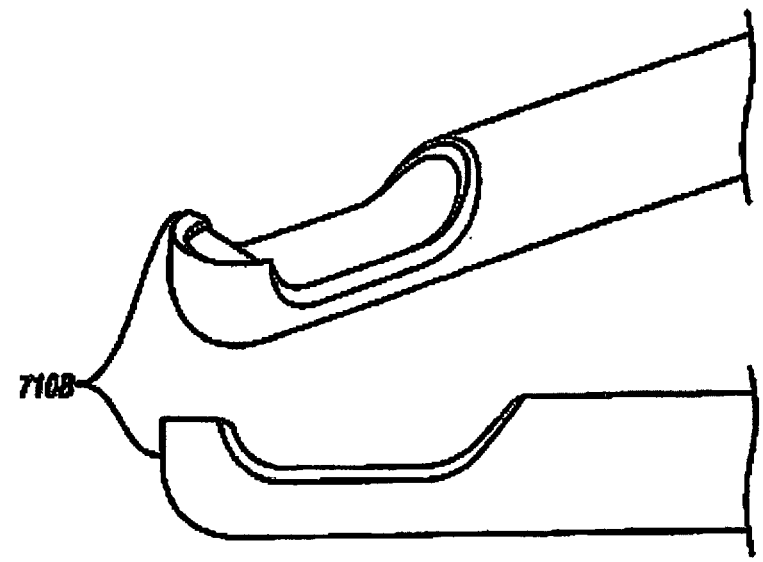
FIG. 7B shows a perspective view and a side view of a customized tip comprising a cup curette tip shaft.
Figure 7C:
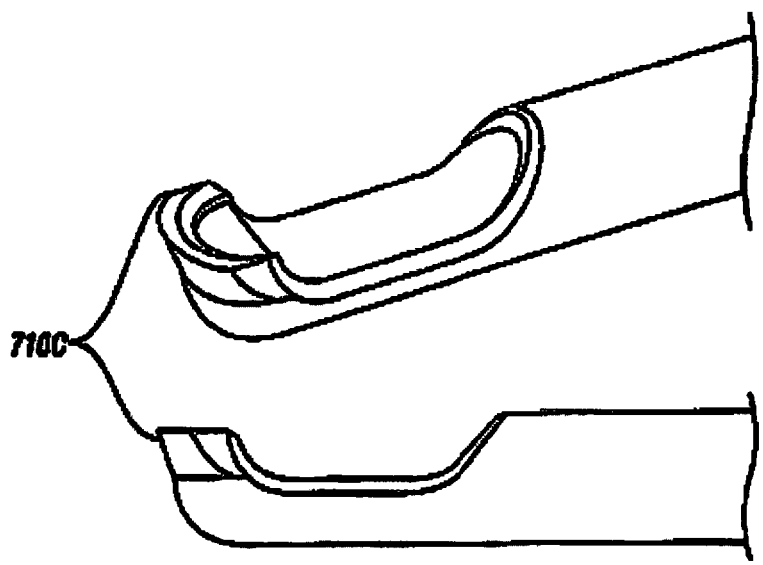
FIG. 7C shows a perspective view and a side view of a customized tip comprising a modified cup curette tip shaft.

FIGS. 7A-7C show a variety of different designs for customizable tips, according to another aspect of the present disclosure. Each of these customizable tips may function in the manner set forth above, or in other ways that will be readily understood by one of ordinary skill in the art. For example, FIG. 7A shows a serrated curette tip 710A which may be useful for gentle endplate scraping. FIG. 7B shows a cup curette tip 710B which may be useful for performing scraping via a pulling motion. FIG. 7C shows a modified cup curette tip 710C which may be useful for scraping via a pushing or pulling motion. It should be noted that it will be readily understood by one of ordinary skill in the art that the disclosure need not be so limited. The customizable tips set forth in the present disclosure may include any scraping instrument which may facilitate the severing of tissue by scraping.

Figure 8A:
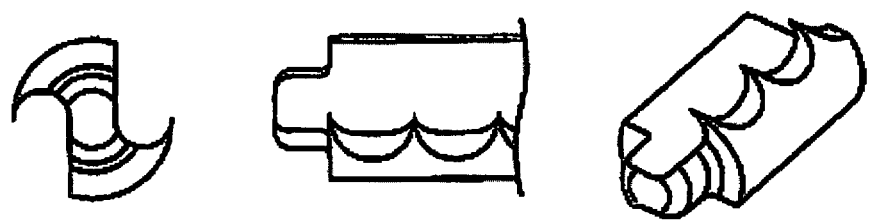
FIG. 8A shows a front view, a top view, and a perspective view of a customized cutter comprising a craw cutter.
Figure 8B:
FIG. 8B shows perspective and side views of a customized cutter comprising a bullet tip serrated cutter.
Figure 8C:
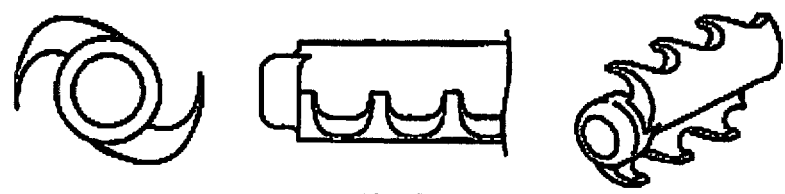
FIG. 8C shows a front view, a top view, and a perspective view of a customized tip comprising a tornado cutter.
Figure 8D:
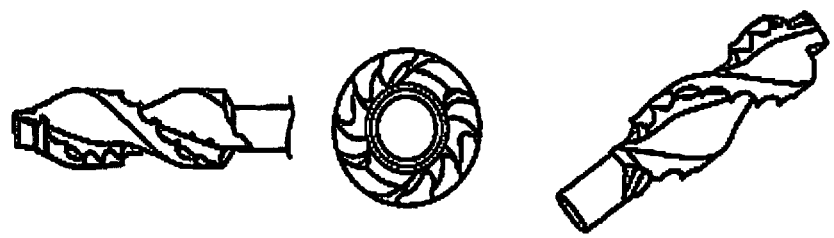
FIG. 8D shows a front view, a top view, and a perspective view of a customized cutter comprising a cyclone cutter.

According to another aspect of the present disclosure, FIGS. 8A-8D show a variety of different designs for cutting instruments which may be part of, or coupled to, for example, the threaded shaft 360 (shown in FIGS. 6A-6C). FIG. 8A shows various views of an example of a craw cutter; FIG. 8B shows various views of an example of a bullet tipped serrated cutter; FIG. 8C shows various views of an example of a tornado cutter; and FIG. 8D shows various views of an example of a cyclone cutter. It is noted that it will be readily understood by one of ordinary skill in the art that the disclosure need not be so limited. The customizable tips set forth in the present disclosure may include any cutting instrument which may facilitate the severing of tissue.

Figure 9:
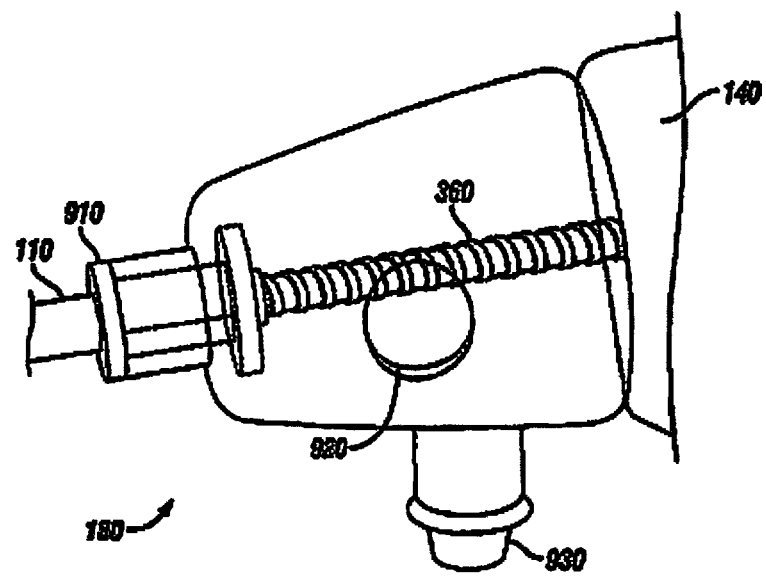
FIG. 9 shows a collection chamber that may be coupled to a tissue removal device, according to a further aspect of the present disclosure.

FIG. 9 shows an example of a collection chamber 130 according to an aspect of the present disclosure. The collection chamber 130 may include a connector 910, pluggable hole 920 and a pluggable port 930. The collection chamber 130 may include at least a partial enclosure that may be made of a transparent material in order to provide a surgeon with the ability to see through collection chamber 130. The material may include, but it is not limited to, e.g., plastic, glass, plexiglass, acrylic glass, etc. This provides a surgeon with the ability to inspect the contents of collection chamber 130 in order to verify the effectiveness of a procedure. It will be readily understood by one of ordinary skill in the art that collection chamber 130 of the present disclosure need not be so limited. The collection chamber 130 may be made of any material, e.g., transparent or non-transparent, that is capable of serving as at least a partial enclosure where tissue, severed by a tissue removal device 100, may be deposited with the aid of an auger-like suction mechanism.

Collection chamber 130 may include a connector 910. The connector 910 may be, for example, integrally formed as a single piece with the collection chamber 130, integrally formed as a single piece with the outer shaft 110, integrally formed as a single piece with the collection chamber 130 and the outer shaft 110, or provided as a separate component that may be attached to the collection chamber 130 and outer shaft 110. Connector 910 may include a pass-through opening to allow the threaded shaft 360 to extend through the connector 910 and into the outer shaft 110, with access to the collection chamber 130 in order to deposit tissue severed and removed by tissue removal device 100. As such connector may serve as a tunnel allowing threaded shaft 360 to extend from the surgical site, through outer shaft 110, and into the collection chamber 130.

Collection chamber 130 may include a pluggable hole 920. During operation of the tissue removal device 100, a plug (not shown) may be inserted into pluggable hole 920 in an attempt to create an enclosure which collects tissue that is severed and removed by the tissue removal device 100. However, after (or while) the procedure is performed, the plug may be removed from pluggable hole 920, thereby providing a surgeon with access to the sample residing in collection chamber 130. With the plug removed, a surgeon may then perform a biopsy of the collected tissue through pluggable hole 920.

Collection chamber 130 may include a pluggable port 930. When tissue removal using the disclosure's auger-like suction is being performed, pluggable port 930 may be sealed with a plug (not shown), where the auger-like suction is implemented without suction based on generated airflow. However, alternatively, or in combination, pluggable port 930 may be unsealed (i.e., unplugged) and coupled to a machine (such as, e.g., a vacuum, a pump, or the like) which generates airflow based suction. The collection chamber 130 provides the versatility for a surgeon to be able to supplement the auger-like suction used to remove severed tissue with a conventional surgical suction unit based on generated airflow. Coupling a conventional, surgical suction unit via pluggable port 930 may be particularly advantageous for surgeons who utilize, e.g., saline solution in the tissue removal process, wherein the conventional surgical suction unit may be used to remove, e.g., the saline solution.

FIG. 10 shows an example of a tissue removal system 1000, which includes power connections and the tissue removal device. In the tissue removal system 1000, the tissue removal device may be powered by a battery pack 1020 and include an on/off toggle switch 1010. The tissue removal system may include, e.g., a stepping motor, or any other driving mechanism that is capable of precise and quick response and control to drive or revolve the threaded shaft 360. Tissue removal system 1000 may also include a pedal 1030 which may be used to vary the speed with which the threaded shaft revolves. While an aspect of the disclosure provides that tissue removal device may be powered by a battery pack, it is noted that the tissue removal system 1000 may include other power supply means, including, e.g., electric power received from residential or commercial power supplies via, e.g., a power cord and plug 1040.

Figure 11A:
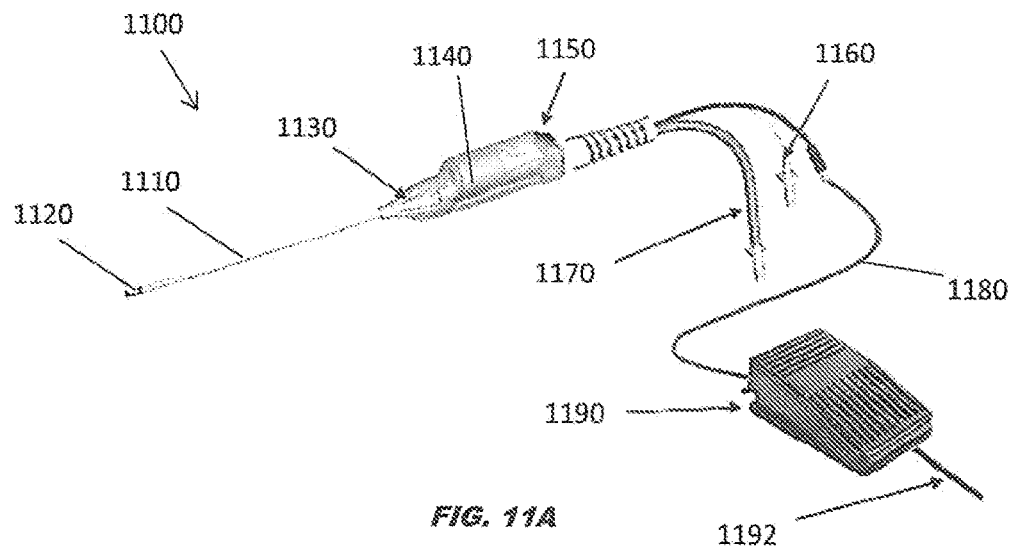
FIG. 11A shows an alternative tissue removal system suitable for use with a tissue removal device.
Figure 11B:
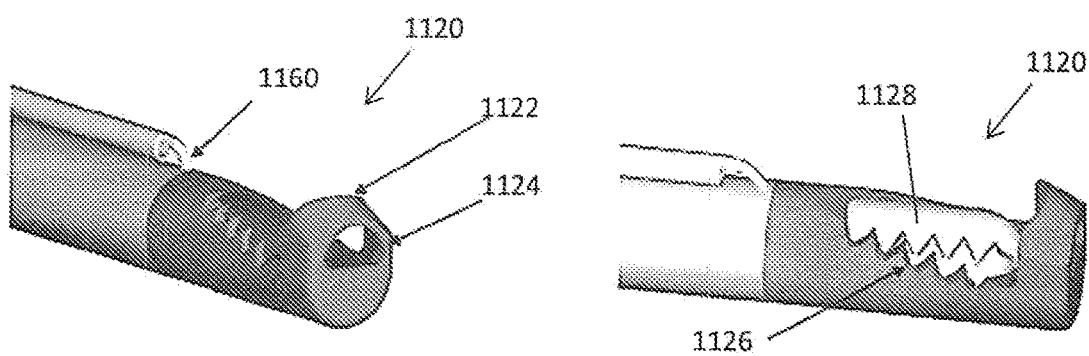
FIG. 11B shows a close-up perspective view of one embodiment of a tissue removal device.

FIG. 11A provides an alternative embodiment of a tissue removal system 1100, which enables the user to remove any desired area of the intervertebral disc. Similar to tissue removal system 1000, tissue removal system 1100 may include an outer shaft 1110 attached to a handle 1140. The outer shaft 1110 may be in the form of a hollow tube extending from a first end to a second end. As shown in FIG. 11B, a distal end of the outer shaft 1110, opposite the handle 1140, may terminate with a removable tip 1120. An auger or inner shaft 1112, best seen in FIG. 11D, may extend through the center of the outer shaft 1110. The inner shaft 1112 may operably attach to the handle 1140 to allow for rotation of the shaft 1112. A distal end of the inner shaft 1112 may terminate as a cutter 1128, which may be positioned within the tip 1120. Any cutter or curette discussed herein may be used.

Figure 11C:
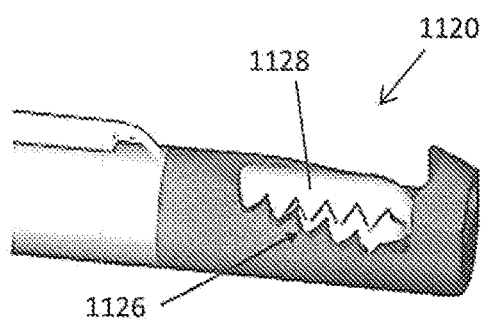
FIG. 11C shows an alternative close-up perspective view of the tissue removal device of FIG. 11B including a cutter.
Figure 11D:
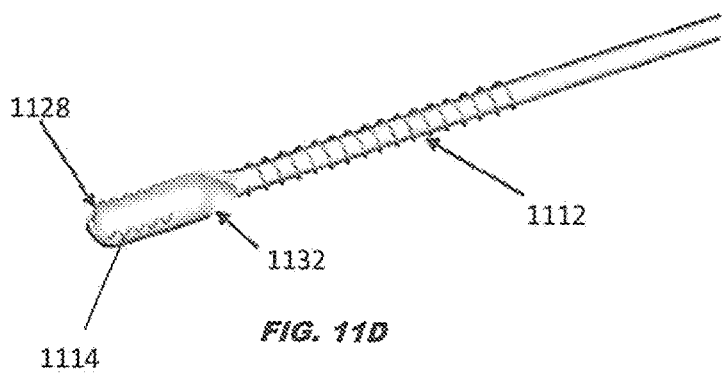
FIG. 11D shows a perspective view of the cutter portion of the tissue removal device.

As shown in FIGS. 11B and 11C, the removable cutter tip 1120 may be provided with several features to enhance cutting and removal of the disc material. The tip 1120 may include a straight or angled blunt distal end. The tip 1120 may include a sharp curette 1122. The sharpened curette 1122 may provide for tactile feedback to the surgeon when the vertebral endplates are prepared. The tip 1120 includes an open window 1124 in the distal end to prevent excessive soft tissue from building up in the cutting area. The window 1124 may be semi-spherical in shape, as shown, or of any other suitable size, shape, and dimension. The cutter 1128 is positioned within the tip 1120 such that when the cutter 1128 rotates, it cuts the disc material and chops the disc material into small particles. The cutter 1128 may have an elongated cupped shape or c-shape with a plurality of teeth 1114 extending from one or more side surfaces. For example, the sharp teeth 1114 of the cutter 1128 may be configured to rotate at high speeds to catch and cut the disc material. The tip 1120 may also include a plurality of teeth 1126. Preferably, the teeth 1126 of the tip 1120 may be angled and/or sloped, which may provide a scissor-like or shearing-type effect when the cutter 1128 rotates against the teeth 1126 of the tip 1120.

As shown in FIG. 11A, the tissue removal system 1100 includes an irrigation tube 1160, a suction tube 1170, and a power cord 1180, which extend from a proximal end of the handle 1140. The irrigation tube 1160 may provide saline water, for example, to the site of the disc removal. In addition, the irrigation tube 1160 may be provided with a diffuser, for example, when exiting the outer shaft 1110 to prevent clogging from soft tissue particles. The suction tube 1170 causes suction through the outer tube 1110, which acts as a suction channel. The suction may be supplied, for example, by a vacuum source such as a vacuum pump or vacuum line. As would be recognized by those skilled in the art, the tissue removal system 1100 may include power cord 1180, which connects to a foot pedal 1190 to enable hands free operation of the instrument 1100. The foot pedal 1190 can connect via cord 1192 to a wall outlet or battery, for example. The instrument 1100 may be provided with a switch 1150, for example, to turn the cutter 1128 on and off.

By way of example, the cutter 1128 may be operated as follows. When the cutter 1128 cuts and forms the disc material into small particles, the material is able to exit through a conical exit path 1132 in the cutter 1128 to provide the tissue with an easy removal system when the cutter 1128 rotates. The inner shaft 1112 may have one or more threaded sections which function as an auger to convey the tissue particles away from the cutter 1128. In addition, the tissue removal system 1100 may include a collection chamber 1130, for example, positioned at a distal end of the handle 1140, for collection of the disc material. The collection chamber 1130 may have an indication window for visual confirmation of removal of the disc material. The auger action and/or suction work to convey the collected material through the conical exit path 1132, through the space between the inner and outer shafts 1112, 1110, and to the collection chamber 1130 without clogging.

Figure 12A:
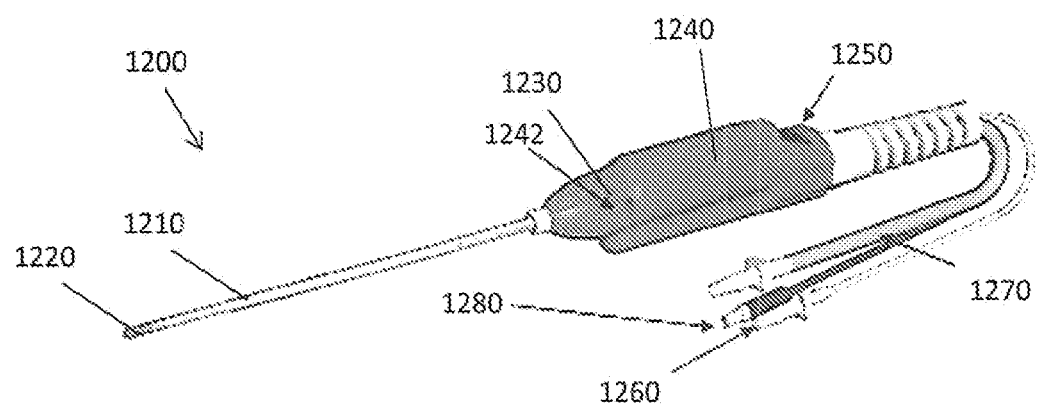
FIG. 12A shows an alternative tissue removal system suitable for use with a tissue removal device having a substantially straight cutting tool.
Figure 12B:
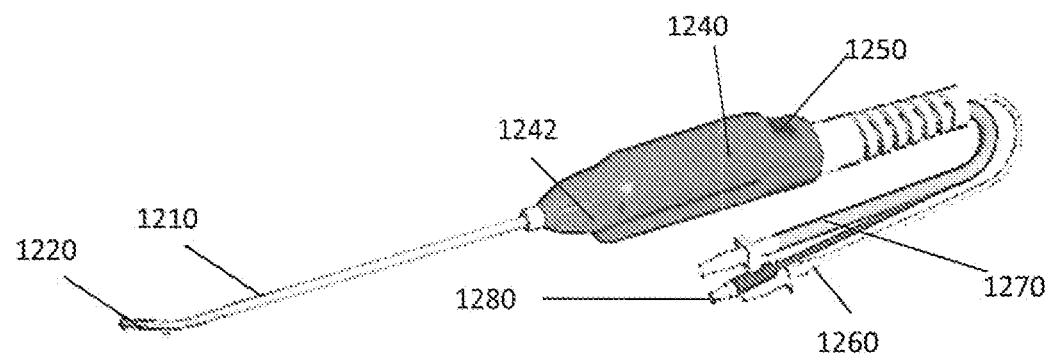
FIG. 12B shows an alternative tissue removal system suitable for use with a tissue removal device having a curved cutting tool.
Figure 12C:
FIG. 12 C shows a foot petal suitable for use with the tissue removal system.
FIG. 12D is a close-up perspective view of the tissue removal device.
FIG. 12E shows an alternative close-up perspective view of the tissue removal device of FIG. 12D including a cutter.
FIG. 12F is a partial cut-away view of a substantially straight tissue removal device.
FIG. 12G is a partial cut-away view of a curved tissue removal device.

FIGS. 12A and 12B provide alternative embodiments of a tissue removal system 1200, which is substantially similar to tissue removal system 1100. FIG. 12A depicts tissue removal system 1200 with a straight shaft cutting tool and FIG. 12B depicts tissue removal system 1200 with an angled-tip cutting tool. In particular, tissue removal system 1200 may include an outer shaft 1210 with removable cutter tip 1220; an inner shaft 1212 extending through the center of the outer shaft 1210 terminating as a cutter 1228; and a handle 1240 having collection chamber 1230 with an indication window 1242 for visual confirmation of disc material removal, on/off switch 1250, and irrigation tube 1260, suction tube 1270, and power cord 1280 extending therefrom. As shown in FIG. 12C, the power cord 1280 may connect to foot pedal 1290 for actuation and a power cable line 1292 for wall outlet or battery connection.

Figure 12D:
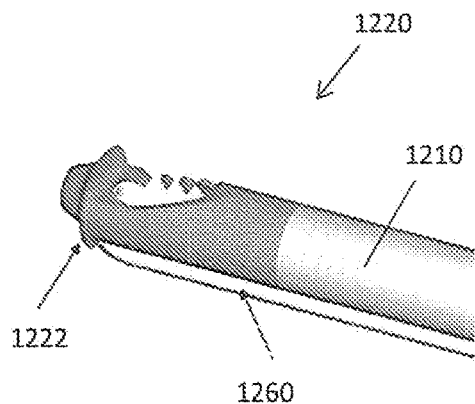
Figure 12E:
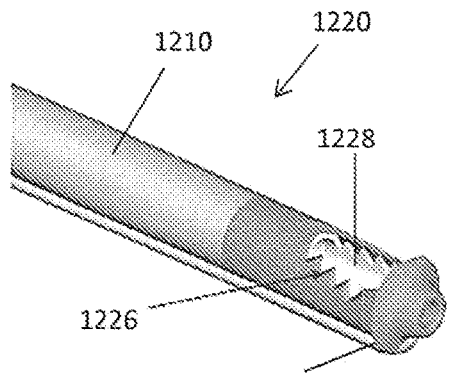

As shown in FIGS. 12D and 12E, the removable cutter tip 1220 may include alternative features to enhance cutting and removal of the disc material. The tip 1220 may include a blunt distal end, for example, with an indentation or recess at the distal-most point. The tip 1220 may include a sharp curette 1222, which extends radially outward therefrom. The sharp curette 1222 may form a lip extending around the entire circumference of the tip 1220. The sharp curette 1222 may be inset a distance from the distal-most point. The curette 1222 may be configured to cut annulus effectively and provide tactile feedback to the surgeon as the vertebral endplates are prepared. The cutter 1228 is positioned within the tip 1220 such that when the cutter 1228 rotates, it cuts the disc material and chops the disc material into small particles. The cutter 1228 may have an elongated cupped shape or c-shape with a plurality of teeth 1214 extending from one or more side surfaces. The tip 1220 also includes a plurality of teeth 1226, for example, in the form of sloped teeth designed to provide a scissor-like shearing effect when the cutter 1228 rotates against the cutter tip 1220.

Figure 12F:
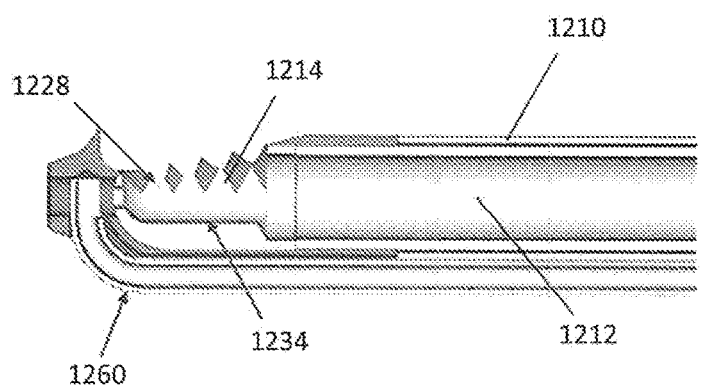
Figure 12G:
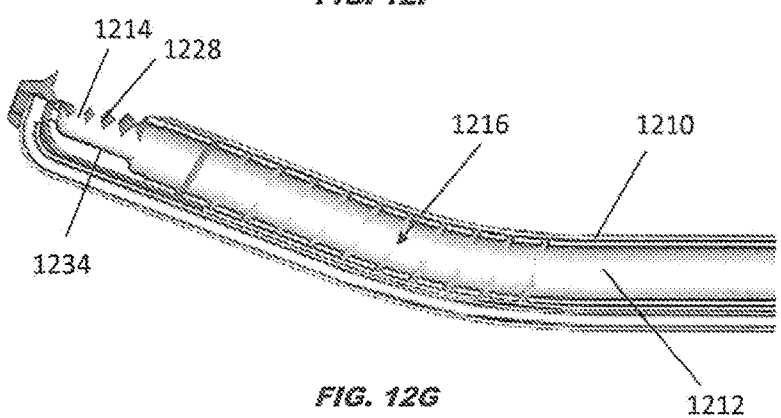

As best seen in FIGS. 12F and 12G, a base or bed 1234 of the cutter 1228 may be offset from the outer tube 1210, for example, to provide an enlarged gap relative to the outer tube 1210. In particular, the base 1234 of the cutter 1228 may create a non-coaxial exit path for the disc material in the end of tip 1220. The non-coaxial space may be configured to produce smaller tissue than inner tube area (e.g., the space between the inner and outer shafts 1212, 1210) so that the tissue particles do not clog the inner tube area.

If desired, irrigation tube 1260 may provide saline water, for example, through an end of the irrigation tube 1260 within the tip 1220. As water hits the cylindrical opening in the inner distal tip 1220, some water may be pumped outside of the tip 1220 in order to provide moisture at the disc cutting area. Suction from suction tube 1270 may convey water and collected material through the cutter tip 1220 to the collection chamber 1230, for example.

FIGS. 12F and 12G depict partial cut-away views of a substantially straight tissue removal device and curved tissue removal device, respectively. The substantially straight version (FIG. 12F) may have a substantially straight inner shaft 1212 and substantially straight outer shaft 1210, which may be substantially rigid, for example. The curved version (FIG. 12G) may have a curve, angle, or bend, for example, proximate to the distal end of the inner shaft 1212 and outer shaft 1210. The curve or angle may be provided by a spring region 1216 in the inner shaft 1212 to bend and rotate the shaft 1212. The spring region 1216 may be in the form or a relief or spiral cut, for example, in an outer surface or inner surface of the inner shaft 1212. The outer shaft 1212 can be formed of a flexible or deformable material to allow for the inner shaft 1212 to curve or angle the relative position of the cutter tip 1220 relative to a longitudinal axis of the outer shaft 1212.

By way of example, for either the straight or curved version, the cutter 1228 shears and cuts the disc material into small particles. Irrigation tube 1260 may provide saline water, for example, to the site of the disc removal. The disc material then exits into the enlarged space between the inner shaft 1212 and the outer shaft 1210. The material is further formed into smaller particles and enters into the space between the inner and outer shafts 1212, 1210. The suction works to convey the tissue particles away from the cutter 1228. The conveyed material travels away from the cutters 1220, 1228, for example, to collection chamber 1230.

The disclosure provides numerous advantages over conventional devices. In light of the disclosure, there is no longer a need for costly capital equipment required to power a tissue removal device. Additionally, the disclosure may be disposable and come in sterile packaging allowing the disclosure to be used by surgeons who may not have access to all methods required for continuously sterilizing equipment. Additionally, the window cut (or formed) into the handle, allows a surgeon to see the height of a blade, thereby providing surgeons with confidence that they have expanded and/or contracted the blade to the correct height. And, the auger-like suction mechanism ensures that the suction mechanism will not clog and bind up the cutting shaft.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A method for removing tissue using a tissue removal device comprising an outer shaft having a removable tip attached thereto and a rotatable inner shaft extending through the outer shaft and having a cutting portion extending from the inner shaft, the method comprising:
    accessing an area for tissue removal;
    cutting a portion of tissue at a surgical site by rotating the cutting portion of the inner shaft; and
    conveying the cut portion of tissue away from the surgical site through a space between the outer shaft and the inner shaft
    wherein the tip includes a curette in the form of a lip radially extending outward around an entire circumference of the tip,
    wherein the lip has a diameter greater than a diameter of a distal end of the tip.

2. The method of claim 1, wherein a portion of the inner shaft is angled.

3. The method of claim 2, wherein the inner shaft includes a spring region in the form or a relief or spiral cut to angle the inner shaft.

4. The method of claim 1, wherein the inner shaft is substantially straight.

5. The method of claim 1, wherein a base of the cutting portion is offset relative to an outer diameter of the outer shaft to allow an enlarged gap between the cutting portion and the outer shaft.

6. The method of claim 5, wherein the enlarged gap creates a non-coaxial exit path for the cut portion of the tissue in the tip.

7. The method of claim 1, wherein the tip includes a blunt distal end, and an open window in the distal end.

8. The method of claim 1, wherein the tip includes a plurality of teeth configured to provide a scissor-like effect when the cutting portion rotates against the plurality of teeth.

9. The method of claim 1, wherein the cut portion of tissue is conveyed via suction.

10. The method of claim 1, wherein at least a portion of the inner shaft is threaded to enhance transportation of the cut portion of tissue in an auger-like manner through the tissue removal device.

11. A method for removing tissue, the method comprising:
    accessing a surgical site for tissue removal;
    providing a tissue removal device for removing tissue, the tissue removal device comprising: an elongate outer shaft having an opening extending therethrough, an inner shaft extending through the outer shaft and creating an opening between the inner shaft and the outer shaft, and a cutting portion extending from the inner shaft that is configured to remove a tissue sample from a surgical site when rotated;
    rotating the cutting portion of the inner shaft to remove tissue from the surgical site; and
    conveying the tissue through the opening between the inner shaft and the outer shaft and away from the surgical site
    wherein the tip includes a curette in the form of a lip radially extending outward around an entire circumference of the tip,
    wherein the lip has a diameter greater than a diameter of a distal end of the tip.

12. The method of claim 11, wherein a portion of the inner shaft is angled.

13. The method of claim 12, wherein the inner shaft includes a spring region in the form or a relief or spiral cut to angle the inner shaft.

14. The method of claim 11, wherein a base of the cutting portion is offset relative to an outer diameter of the outer shaft to allow an enlarged gap between the cutting portion and the outer shaft.

15. The method of claim 14, wherein the enlarged gap creates a non-coaxial exit path for the cut portion of the tissue in the tip.

16. The method of claim 11, wherein the tip includes a blunt distal end, and an open window in the distal end.

17. The method of claim 11, wherein the tip includes a plurality of teeth configured to provide a scissor-like effect when the cutting portion rotates against the plurality of teeth.

18. A method for removing tissue using a tissue removal device comprising an outer shaft having a removable tip attached to the outer shaft, a rotatable inner shaft extending through the outer shaft and having a cutting portion extending from the inner shaft, a base of the cutting portion being offset relative to an outer diameter of the outer shaft to allow an enlarged gap between the cutting portion and the outer shaft, the method comprising:
- accessing an area for tissue removal;
- cutting a portion of tissue at a surgical site by rotating the cutting portion of the inner shaft;
- conveying the cut portion of the tissue through the enlarged gap providing for a non-coaxial exit path for the cut portion of the tissue in the tip; and
- conveying the cut portion of tissue away from the surgical site through a space between the outer shaft and the inner shaft
- wherein the tip includes a curette in the form of a lip radially extending outward around an entire circumference of the tip,
- wherein the lip has a diameter greater than a diameter of a distal end of the tip.

* * * * *